(12) United States Patent
Pouteau et al.

(10) Patent No.: US 10,634,585 B2
(45) Date of Patent: Apr. 28, 2020

(54) SYSTEM FOR ANALYZING A LIQUID SAMPLE

(71) Applicant: AVALUN, Grenoble (FR)

(72) Inventors: Patrick Pouteau, Meylan (FR); Vincent Poher, Guines (FR); Paul Laurens, Gillonnay (FR)

(73) Assignee: AVALUN, Grenoble (FR)

( * ) Notice: Subject to any disclaimer, the term of this patent is extended or adjusted under 35 U.S.C. 154(b) by 454 days.

(21) Appl. No.: 15/198,314

(22) Filed: Jun. 30, 2016

(65) Prior Publication Data

US 2017/0003202 A1 Jan. 5, 2017

(30) Foreign Application Priority Data

Jul. 3, 2015 (FR) ..................................... 15 56307

(51) Int. Cl.
| | |
|---|---|
| *G01N 1/10* | (2006.01) |
| *B01L 3/00* | (2006.01) |
| *B01L 9/00* | (2006.01) |
| *G01N 21/49* | (2006.01) |
| *G01N 21/78* | (2006.01) |
| *G01N 33/487* | (2006.01) |

(52) U.S. Cl.
CPC ................ *G01N 1/10* (2013.01); *B01L 3/508* (2013.01); *B01L 9/50* (2013.01); *G01N 21/49* (2013.01); *G01N 21/78* (2013.01); *G01N 33/48785* (2013.01); *B01L 2200/025* (2013.01); *B01L 2300/0654* (2013.01); *B01L 2300/0848* (2013.01); *B01L 2300/18* (2013.01); *G01N 2201/062* (2013.01); *G01N 2201/0612* (2013.01)

(58) Field of Classification Search
CPC .......... G01N 1/10; G01N 21/78; G01N 21/49; B01L 3/508; B01L 9/50
See application file for complete search history.

(56) References Cited

U.S. PATENT DOCUMENTS

| | | | | |
|---|---|---|---|---|
| 6,009,632 A | * | 1/2000 | Douglas | ............. G01N 21/8483 33/562 |
| 2004/0007585 A1 | * | 1/2004 | Griffith | ............ G01N 33/48757 221/232 |

(Continued)

FOREIGN PATENT DOCUMENTS

| | | |
|---|---|---|
| CN | 1902484 | 1/2007 |
| FR | 3003033 | 9/2014 |

(Continued)

*Primary Examiner* — Matthew D Krcha
(74) *Attorney, Agent, or Firm* — Occhiuti & Rohlicek LLP (57) ABSTRACT

The invention relates to a system for analyzing a liquid sample, including an analysis device comprising a casing including a through-opening leading into a housing adapted to receive a portion of a collecting device and extending longitudinally from the opening along an axis of insertion of the collecting device. The analysis system further includes a collecting device comprising a main body extending along a longitudinal axis and including a fluid chamber adapted to be inserted in the housing along the insertion axis and a receiving surface intended to receive the liquid sample extending substantially orthogonally relative to the axis of the main body.

20 Claims, 6 Drawing Sheets

(56) References Cited

U.S. PATENT DOCUMENTS

| | | | |
|---|---|---|---|
| 2006/0051738 A1* | 3/2006 | Zweig | C12Q 1/005 435/4 |
| 2007/0202007 A1 | 8/2007 | Augstein et al. | |
| 2008/0025872 A1* | 1/2008 | Dykes | A61B 5/14546 422/68.1 |
| 2010/0267049 A1* | 10/2010 | Rutter | G01N 21/6428 435/7.1 |
| 2014/0081093 A1* | 3/2014 | Kim | A61B 5/0075 600/301 |
| 2016/0022189 A1 | 1/2016 | Pouteau et al. | |

FOREIGN PATENT DOCUMENTS

| | | |
|---|---|---|
| WO | WO98/19159 | 5/1998 |
| WO | WO2005/088319 | 9/2005 |

* cited by examiner

Fig.6 of the casing. The housing is disposed in the interior space and extends longitudinally from the opening along an insertion axis for receiving the collection device. A detection-and-analysis device detects and analyzes a representative parameter of the liquid sample.

SYSTEM FOR ANALYZING A LIQUID SAMPLE

RELATED APPLICATIONS

Under 35 USC 119, this application claims the benefit of the Jul. 3, 2015 priority date of French application FR1556307, the content of which is herein incorporated by reference in its entirety.

FIELD OF DISCLOSURE

This disclosure relates to analysis of liquid samples, and in particular, to devices to facilitate such analysis.

BACKGROUND

It is known to detect analytes in various liquids. This is typically carried out by collecting a liquid in a collection device and inserting that collection device, together with the liquid to be analyzed, into an analysis apparatus. Within the apparatus, some type of sensor is present to measure some property of the liquid. An example of a sensor is an optical sensor.

Suitable liquids for analysis include liquids of biological origin, such as blood, saliva, urine, interstitial liquid, or even any other type of liquid where the aim is to detect and to analyze a representative parameter.

SUMMARY OF THE INVENTION

In one aspect, the invention features a liquid-sample analysis system that includes an analysis device and a collection device, a portion of which is inserted into a housing of the analysis device.

The analysis device includes a casing that delimits an interior space and that includes an opening into the housing. The housing is disposed in the interior space and extends longitudinally from the opening along an insertion axis for receiving the collection device. A detection-and-analysis device detects and analyzes a representative parameter of the liquid sample.

The collection device comprises a body, a receiving surface, a measurement chamber (hereafter referred to as simply a "chamber"), and an orifice. The body extends along a longitudinal axis of the collection-device and is adapted to be inserted into the housing along the insertion axis. When the collection device's body has been inserted into the housing, the receiving surface remains outside the housing to receive the liquid sample. The receiving surface extends along a direction that has a component that is orthogonal to the longitudinal axis. The orifice provides fluid communication into the chamber.

In some embodiments when the collection device's body has been inserted into the housing, the distance between the orifice and the chamber is approximately equal to the distance between the opening of the housing and the chamber. Among these are embodiments in which this distance is less than or equal to two centimeters.

In other embodiments, the collection device includes a collection part assembled to the body. A surface of the collection part forms the receiving surface. The collection part contacts a wall of the casing at an edge of the housing's opening when the body of the collection device has been inserted into the housing.

In some embodiments, the casing includes an upper wall and a lower wall connected to each other by a lateral wall having a dimension that is less than the dimensions of the upper and lower walls. The housing's opening is situated at the upper wall of the casing. The housing extends in a direction that is substantially orthogonal to the upper wall in the direction of the lower wall. Among these are embodiments in which the casing's upper wall includes a display screen.

In some embodiments, the analysis device further includes a bearing surface that is fixed relative to the housing and that is disposed so as to delimit, in part, the housing. It does so by extending parallel to the insertion longitudinal-axis of the housing. When the collection device's body has been inserted into the housing, the bearing surface contacts that portion of the body that contains the chamber.

Among these are embodiments are those in which the detection and analysis device includes an optical sensor situated on a side of the bearing surface opposite the housing. In such embodiments, the bearing surface is transparent to light beams coming from the chamber when the body of the collection device is inserted in the housing.

Other embodiments are those in which the detection-and-analysis device includes an optical sensor situated at a longitudinal distance relative to the opening of the housing, wherein the longitudinal distance is less than or equal to two centimeters.

In some embodiments, the analysis device further includes a locking-and-disengagement device that is adapted to retain the body in a locking position inside the housing. Such a locking-and-disengagement device includes a disengagement member and a locking member. The disengagement member is adapted to exert an exit force on the body when the body is inserted into the housing in a direction parallel to the insertion longitudinal-axis of the housing and oriented toward the opening of the housing. The locking member includes at least one abutment portion adapted to be in contact with a bearing portion of the body when the body is inserted into the housing in the locking position so as to immobilize the collection device, which becomes subjected to the exit force along the longitudinal axis of the housing.

Also among the embodiments are those in which the body includes a lateral shoulder that forms the bearing portion of the collection device's body. The lateral shoulder is situated between a central portion of the body, which contains the chamber, and a distal end of the body. The distal end of the body is distal relative to the receiving surface.

In some embodiments, the analysis device further includes a spacer disposed longitudinally along a border of the bearing surface and projecting relative to the bearing surface in the direction of the housing. The spacer has longitudinal ends that are beveled so as to space the body relative to the bearing surface upon movement of the bearing surface in the housing along the insertion axis.

In other embodiments, the locking member is mobile relative to the housing along a direction that is substantially transverse to the longitudinal axis of the housing. In these embodiments, the locking member is adapted to exert a bearing force on the body in the direction of the bearing surface when the body is inserted in the housing.

In some embodiments, the locking-and-disengagement device includes an unlocking member that, when actuated, causes movement of the locking member so as to break an abutment between the abutment portion of the locking member and the bearing portion of the collection device, thereby leading to withdrawal of the body relative to the housing by the effect of the exit force.

In some embodiments, the detection-and-analysis device includes a light source and an optical sensor disposed on respective opposite sides of the housing along an axis of illumination of the chamber when the body of the collection device is inserted into the housing. In these embodiments, locking member includes a hollow portion positioned between the light source and the optical sensor. As a result, illumination beams propagate along the illumination axis through the hollow portion.

Some embodiments also include a heating element adapted to transmit heat to the chamber via the bearing surface when the body is inserted into the housing and in contact with the bearing surface.

In another aspect, the invention features a method for analyzing a sample using an apparatus as described above. Such a method includes introducing the collection device into the housing, depositing a liquid sample on the collection device's receiving surface so that it contacts the orifice, detecting and analyzing the liquid sample, and withdrawing the collection device from the housing.

Some practices include having a user hand-hold the analysis device during deposition of the liquid sample on the receiving surface.

Other practices include orienting the receiving surface substantially orthogonal to the direction along which gravity acts while depositing the sample on the receiving surface.

BRIEF DESCRIPTION OF THE DRAWINGS

Other aspects, objects, advantages and features of the invention will become more apparent on reading the following detailed description of preferred embodiments thereof given by way of nonlimiting example and with reference to the appended drawings, in which:

FIG. 1b is sectional view of the combination shown in FIG. 1a;

FIG. 2a is a front view of the collection device represented in FIG. 1a;

FIG. 2b is a perspective view showing the male and female portions that form the collection device shown in FIG. 2a;

In the figures and in the remainder of the description, the same references represent identical or similar elements. Moreover, the various elements are not shown to scale in order to make the figures clearer.

DETAILED DESCRIPTION

Figure 1A:
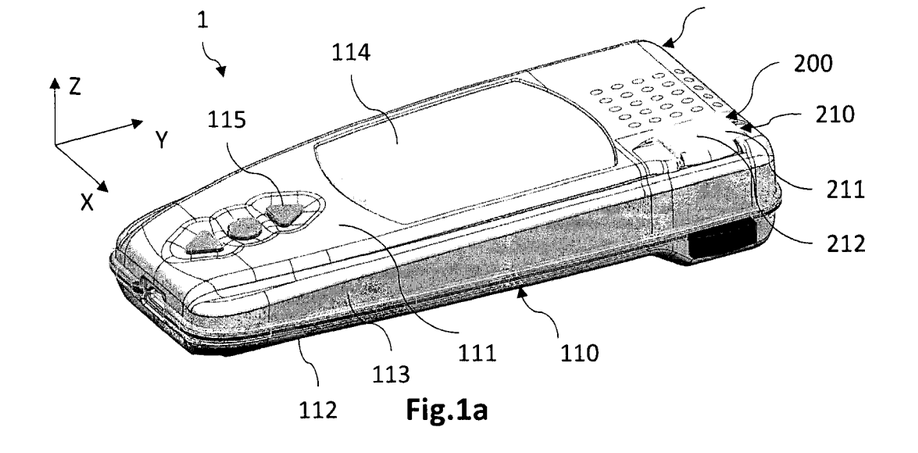
FIG. 1a is a perspective view a combination formed by a collection device that has been inserted into an analysis device.

FIG. 1a shows a liquid-sample analysis system 1 having an analyzer 100 and a collection device 200 that has been inserted into the analyzer 100. The collection device 200 collects the liquid sample that is to be analyzed. Typically, the collection device 200 is disposable.

Throughout the remainder of the description, reference will be made to a three-dimensional frame-of-reference in which an X-axis extends in the direction of the analysis apparatus' width, a Y-axis extends in the direction of its length, and the Z-axis extends in the direction of its thickness.

The analyzer 100 includes an upper wall 111, a lower wall 112, and a lateral wall 113 that together define a casing 110 that delimits the interior space. Within the casing 110 is an electric power source to provide power for operation of various electronic components. A suitable power supply is a battery.

The lateral wall 113 extends all around the contour of the apparatus and connects the upper wall 111 and the lower wall 112 to each other. The height of the lateral wall 111 defines a thickness. In the example shown in the figure, the analyzer 100 has a thickness that is less than its width and also less than its length.

In FIG. 1a, the upper wall 111 and the lower wall 112 are substantially coplanar with the XY plane. The upper wall 111 includes a display screen 114 and keys 115 for selecting various modes of using the apparatus.

Figure 1B:
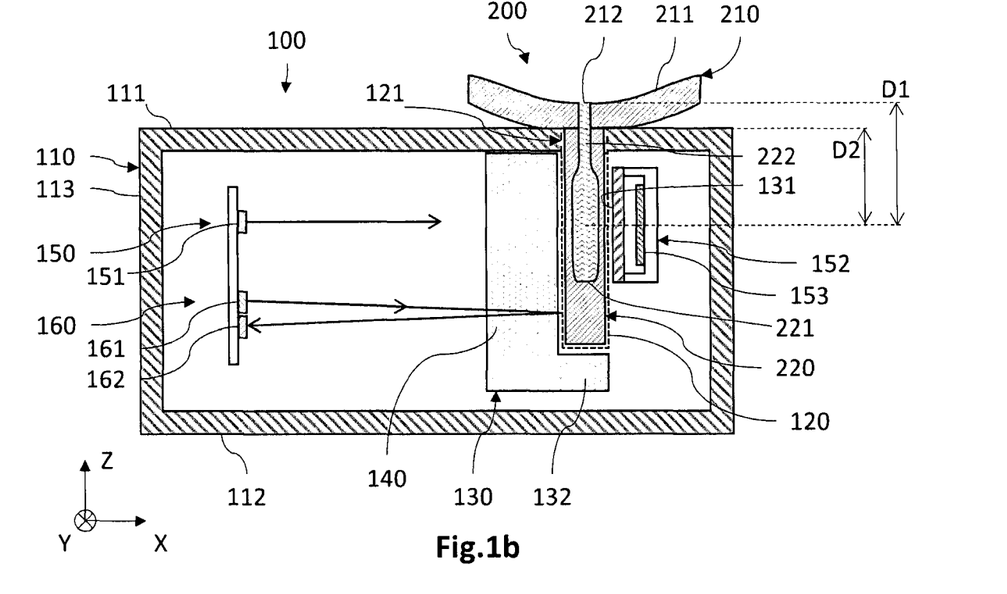

FIG. 1b shows a section in the XZ plane of a part of the analyzer 100 shown in FIG. 1a with the collection device 200 inserted therein.

Within the casing's interior space, there exists a housing 120, a locking-and-releasing device 130, and a detection-and-analysis device 150.

The housing 120 receives a part of the collection device 200 into a position that will enable detection and analysis of the liquid sample. An opening 121 at the level of the casing's upper wall 111 provides communication between the housing 120 and the environment. The housing 120 extends along an insertion axis from the opening 121 towards the lower wall 112.

The locking-and-releasing device 130 locks and releases the collection device 200. It includes a bearing plate 134 (shown in FIG. 6) that supports a bearing surface 131, a locking member 140, and a releasing member 132. The bearing surface 131 extends longitudinally along one side of the housing 120. The locking member 140 is disposed on the side of the housing 120 opposite the bearing surface 131. The releasing member 132 is located facing the lower part of the housing 120, i.e., the distal part of the housing 120 relative to the opening 121.

The detection-and-analysis device 150 detects and analyzes one or more characteristic properties of the liquid sample.

The collection device 200 is inserted into a housing 120 of the analyzer 100. The housing 120 is level with the upper wall 111 so that only a collection part 210 of the collection device 200 can be seen outside the apparatus.

The collection part 210 has an upper surface 211, hereafter referred to as the "receiving surface 211." The receiving surface 211 is what first receives a liquid sample.

In the example shown, the receiving surface 211 is substantially orthogonal to the longitudinal axis of that part of the collection device 200 that is inserted into the housing 120 and to that of the housing 120. However, in some embodiments, the receiving surface 211 is substantially parallel to the same longitudinal axis, notably when the opening is located at the level of the casing's lateral wall 113. The receiving surface 211 includes a collection orifice 212, hereafter referred to as simply the "orifice 212," through which the liquid sample enters the collection device 200.

FIGS. 1a and 1b show an analyzer 100 and a collection device 200 that are adapted to allow insertion of a portion of the collection device 200 into the housing 120 along an insertion axis, or longitudinal axis that is substantially orthogonal to the receiving surface 211.

As used herein, "a receiving surface 211 substantially orthogonal, respectively parallel, to the longitudinal axis of the housing 120, or insertion axis" means that, when the collection device 200 is inserted into the analyzer 100, the receiving surface 211 has a plane tangential to the surface at the level of the orifice 212, substantially orthogonal, respectively parallel, to the insertion axis.

In the particular example shown herein, the collection device 200 includes a collection part 210 and a main body 220, which will hereafter be referred to as the "body 220". The collection part 210 has, at an upper part thereof, a receiving surface 211 that receives the liquid sample. The body 220 extends longitudinally and substantially orthogonally to the collection part 210.

The body's longitudinal axis is substantially orthogonal to a plane tangential to the receiving surface 211 at the level of the orifice 212.

The body 220 includes a chamber 221 in fluid communication with the orifice 212 via a fluid passage 222. As can be seen in FIG. 1b, once the collection device 200 has been inserted into the housing 120, its body 220 engages the casing 110 and its collection part 210 remains outside the casing 110.

In some embodiments, the collection part 210 rests on or otherwise contacts the casing's wall. This promotes more accurate positioning of the collection device 200 along the insertion axis. It also offers a better distribution of mechanical load when the liquid sample is actually being deposited onto the collection part 210.

The detection-and-analysis device 150 includes a detection unit and an analysis unit. The detection unit detects one or more characteristic properties of the sample. Examples of characteristic properties include electrical, chemical, and optical properties.

In the particular embodiment described herein, the detection unit is an optical detector that includes one or more light sources 151 and an optical sensor 152. The light sources 151 can be seen on the left-hand side of FIG. 1b. The optical sensor 152, can be seen in the right-hand side of FIG. 1b.

The light source 151 is disposed to illuminate the chamber 221 as shown in FIG. 1b by directing light along the X direction towards the chamber 221. The light then interacts with whatever is in the chamber 221 and the result of the interaction is received at a photodetector 153 disposed behind the bearing surface 131. As a result, the bearing surface 131 is transparent to the wavelengths of light that either pass through the chamber 221 or that result from the interaction within the chamber 221.

In the illustrated embodiment, no lenses are used. In addition, the locking member 140, which is placed between the light source 151 and the photodetector 153, is configured to avoid blocking or otherwise interfering with light emitted by the light source 151 as it travels toward the chamber 221.

The analyzer 100 processes the measured data and displays pertinent information on the display screen 114.

The analysis unit, which is not explicitly shown, includes a processor and a memory that stores instructions to be used for carrying out data processing steps based on measurements. In some embodiments, the analysis unit also stores data or communicates with one or more external devices. Further embodiments include those in which the analysis unit interfaces with the keys 115.

The particular embodiment shown also includes a reader 160 that optically reads information that has been placed on the collection device's body 200. Such information may have been encoded as a QR code or a Datamatrix code. Examples of suitable information that could be encoded include the type of liquid sample, the type of detection and analysis to be carried out, an expiration date, or a manufacturing batch number.

The reader 160 includes a light source 161 and a photodetector 162, such as a matrix photodetector. In the illustrated embodiment, the photodetector 162 and the light source 160 are on the same side of the casing 110. As such, the reader 160 works in reflection mode. However, it is possible to arrange the parts of the reader 160 to operate in transmission mode instead. In the apparatus described herein, the receiving surface 211 is substantially orthogonal to the longitudinal axis of the body 220 and substantially coplanar with the opening that leads into the recess. As such, it can be seated as close as possible to the casing 110 when the collection device is inserted into the housing 120.

The ability to minimize how much of the collection device 200 sits outside of the analyzer 100 reduces the length of the fluid passage 222 that connects the orifice 212 to the chamber 221. This has the effect of reducing how much liquid has to be collected, since the amount of liquid that fills the fluid passage 222, which is not being analyzed anyway, can be reduced.

Additionally, by reducing how much of the collection device 200 is outside the analyzer 100, it becomes possible to reduce the risk of incorrectly manipulating the collection device 200 during the detection process. Such incorrect manipulation can easily interfere with the detection process and thus cast doubt on the result of the analysis.

The opening 121 that leads into the housing 120 is disposed at the upper wall 111 of the casing 110. The housing 120 extends towards the lower wall 112 in a direction substantially orthogonal to the upper wall 111. In some embodiments, the housing 120 extends in a direction that is within ten degrees of a line normal to the plane defined by the upper wall 111. In other embodiments, the housing 120 extends in a direction that is within twenty degrees of a line normal to the plane defined by the upper wall 111.

In some embodiments, at least a portion of the upper wall 111 forms a dome. In such cases, the housing 120 extends towards the lower wall 112 along a direction that is substantially orthogonal to a plane that is locally tangent to the dome.

In some embodiments, the housing 120 is within twenty degrees of being orthogonal to a plane along which a substantial portion of the casing 110 extends. In other embodiments, the housing 120 is within twenty degrees of being orthogonal to a plane defined by the lower wall 112 of the casing 110. In these embodiments, the upper and lower walls 111, 112 have dimensions along the X and Y axes that are greater than the dimension along the Z axis. In other embodiments, the casing 110 has a length, a width, and a thickness, which is defined by the lateral wall 113, that is much less than either the length or the width.

The process of depositing the liquid sample on the collection surface 211 begins with orienting the collection surface 211 so that it is horizontal. A bearing force typically accompanies the deposition of a liquid sample on the receiving surface 211. Such a bearing force may arise from a patient's finger pressing on the receiving surface 211. Because this bearing force is parallel to the axis of the body 220, the body 220 avoids sustaining torsion. Additionally, when the collection part 210 contacts the casing's wall, any such bearing force can be sustained by the casing 110, thus avoiding mechanical load on the body 220.

The collection part 210 projects transversely relative to the body 220 with its receiving surface 211 having an area that is greater than that of the body's cross section at the level of the chamber 221. The body's narrow dimension permits it to be inserted in a small casing 110, whereas the large area of the receiving surface 211 improves its ability to receive a liquid sample.

In some embodiments, the body's cross section at the measurement chamber 221 is on the order of ten to a few tens of square millimeters while the area of the receiving surface 211 is on the order of one hundred to a few hundred square millimeters. The area of the receiving surface 211 protects the analyzer's surface, and in particular, the opening 121, from overflow as a result of surplus sample volume or from inaccurate deposition of the sample.

When the collection device 200 is inserted into the housing 120, there exists a first plane, a second plane, and a third plane, all of which are parallel. The first plane is a plane that includes the orifice 212. The second plane is a plane that includes the opening 121 into the housing 120. The third plane is a midplane of the measurement chamber 221.

The first and third planes define a first distance D1 therebetween. The second and third planes define a second distance D2 therebetween. These distances are generally less than or equal to two centimeters, and in some embodiments, less than or equal to only one centimeter. The first distance D1 is measured from the orifice 212 along a central axis of the chamber, which extends along the Z-direction. Similarly, the second distance D2 is measured from the opening 121, for example at the surface of the casing's wall, along the same central axis of the chamber.

In some embodiments, the first and second distances D1, D2 are approximately equal. In other embodiments, the difference between the first and second distances D1, D2 is less than or equal to 25% of the greater of the first and second distances D1, D2. In other embodiments, the difference between the first and second distances D1, D2 is less than or equal to 10% of the greater of the first and second distances D1, D2. In other embodiments, the first and second distances D1, D2 differ by the sum of the thicknesses of the collection part 210 and the upper wall 111 of the casing 110.

In some examples, for a first distance equal to ten millimeters, the second distance D2 is equal to eight millimeters. In such examples, the thickness of the collection part 210 is on the order of two millimeters. This greatly reduces the length of the fluid passage 222 that connects the chamber 221 to the orifice 212.

Figure 2A:
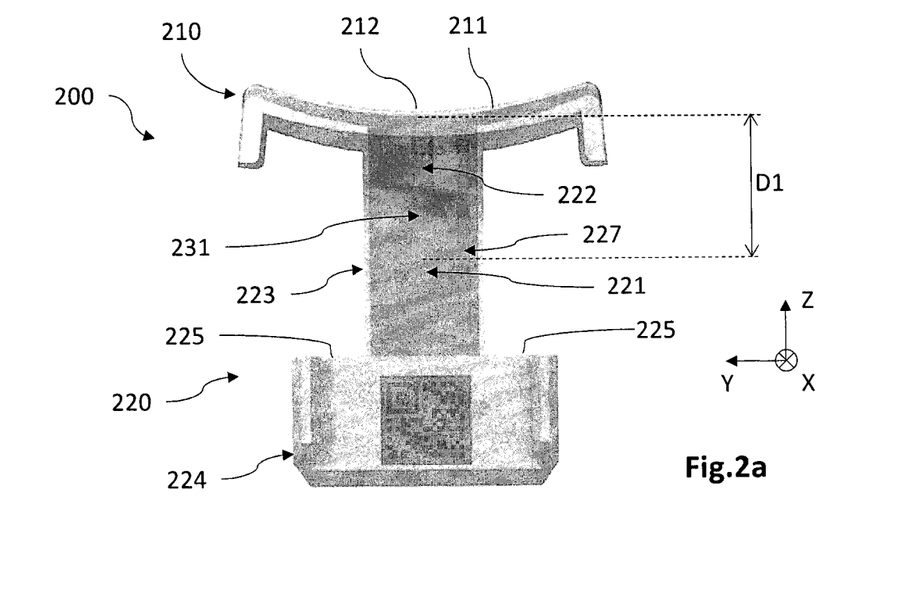

FIG. 2a is a front view of an example of a collection device 200 that is adapted to cooperate with the analyzer 100 by being inserted into and then ejected from the analyzer 100. The collection device 200 is therefore removable from the analyzer 100.

The body 220 has dimensions matching those of the housing 120. As shown in FIG. 2a, the body 220 has a central portion 223 having a first end and a second end. The central portion's first end connects to the collection portion 210. The central portion's second end connects to a heelpiece 224 of the body 220.

The fluid passage 222 extends into the central portion 223 from the collection portion 210. As it does so, it widens along the Y axis to form the measurement chamber 221, which is also within the central portion 223. The widening to form the measurement chamber 221 results in a larger target for illumination and detection.

The heelpiece 224 enables a user to hold and manipulate the collection device 200 more easily. The heelpiece 224 has a width along the Y axis that is greater than that of the central portion 223. In the embodiment shown in FIG. 2a, the lateral wall along the Y axis includes at least one bearing surface 225.

In the embodiment shown in FIG. 2a, a pair of shoulders forms two bearing surfaces 225 that cooperate with the locking member 140 of the analyzer 100.

As used herein, a "shoulder" refers to a sudden variation in the cross section of the body 220 in order to form a bearing surface 225 oriented in the direction of the collecting portion. Some embodiments avoid the use of a shoulder as a bearing surface 225 and instead rely on an opening made in either the central portion 223 or the heelpiece 224. The walls of such an opening would then define a bearing surface 225.

In some embodiments, the heelpiece 224 includes an area for imprinting information, such as a QR code or a Datamatrix code. Among these embodiments are those in which the area is under the chamber 221.

Some embodiments also include a projecting portion that makes it more difficult to make an error in using or manipulating the collection device 200. The illustrated embodiment features two portions that extend transversely to the YZ-plane defined by the heelpiece 224. The housing 120 has a shape that corresponds to the shape of the projecting portion in such a way that it is essentially impossible to insert the collection device 200 into the housing 120 incorrectly.

Figure 2B:
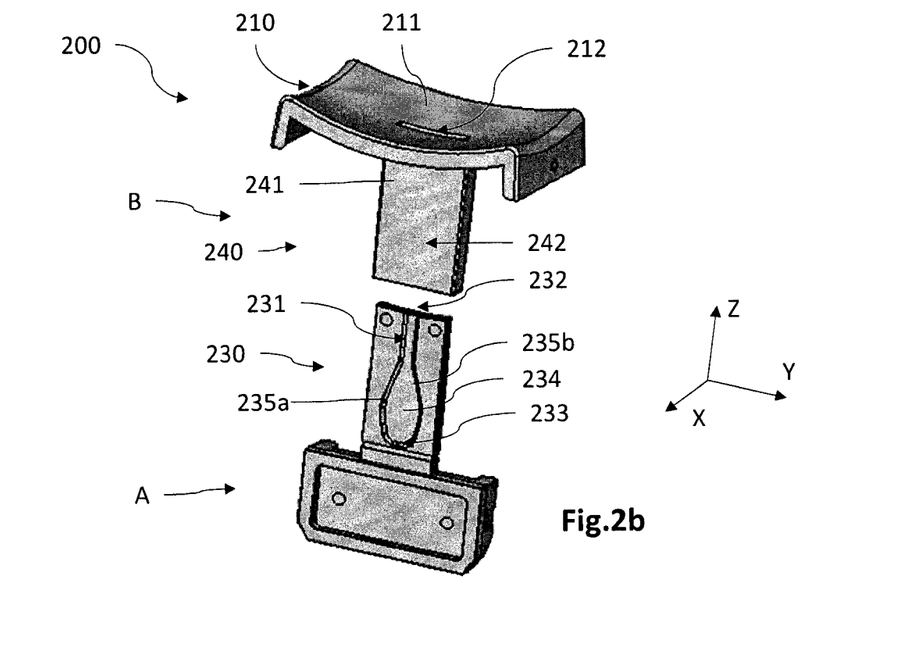

As shown in FIG. 2b, the collection device 200 includes first and second elements A, B that cooperate to render the collection device 200 operational.

The first element A includes a male portion 230 and the second element B includes a female portion 240. The male portion 230 has a longitudinally extending bottom wall 234 that adjoins two opposing lateral walls 235a, 235b to define a recess that that is shaped like the chamber 221. However, it is not fully enclosed because it does not have a cap.

Meanwhile, the female portion 240 features a peripheral wall 241. This peripheral wall 241 forms a cap 242 over the recess to form the measurement chamber 221 once the female portion 240 engages the male portion 230. Thus, inserting the male portion 230 into the female portion 240 forms the measurement chamber 221.

The chamber's channel 231 opens at an inlet 232 to receive a liquid sample. When a liquid sample enters the orifice 212, capillary flow along the channel 231 in the direction of the second end 233 brings it into the chamber 221.

An advantage of having first and second elements A, B is that prior to insertion of the male portion 230 into the female portion 240, there is direct access to the channel's interior and after insertion of the male portion 230 into the female portion 240, the channel 231 becomes fully confined.

The ability to directly access the interior of the channel 231 or at least a portion of its internal surfaces makes it possible to either functionalize or treat the channel's interior. As a result, it is simple to carry out such tasks as depositing, within the channel 231, a dried reagent that is intended to interact with a liquid sample and to do so evenly across as much as the entire length of the channel 231. With the channel 231 being so easily accessible, it becomes possible to accurately position tools for depositing reagents that are to be dried, including freeze-dried. This makes it possible to deposit reagent at precise locations, such as at the inlet or within the channel's interior or at an outlet where the channel 231 meets the chamber 221.

It is not only reagents that can be deposited precisely at any location but also such structures as electrodes or absorbent membranes. Additionally, it is possible to functionalize parts of the channel by chemically bonding substances to the channel's interior, for example by locally immobilizing molecules or biological entities directly to a channel wall by, for example, forming a covalent bond between the molecule or biological entity and the channel's interior. Examples of molecules or biological entities include proteins, sections of DNA, or antibodies.

The engagement of the male and female portions 230, 240 confines the channel 231 with particular effectiveness and limits or even prevents contamination of the external environment by liquid in the channel or entry of pollutants into the channel 231 from the external environment.

In the illustrated example, a plate having a substantially rectangular cross-section forms the male portion 230. However, other cross sections, such as a circular or square cross section can be used. The channel 121 is disposed at the level of the plate's upper longitudinal face. As a result, the channel's inlet 232 discharges onto the plate's transverse end wall.

The channel's longitudinal bottom wall 234 has a cross section whose dimension exceeds that of each of the lateral walls 235a, 235b. This affects the ratio between the width of the channel and its depth, a quantity referred to herein as the channel's "transverse form factor." This transverse form factor is greater than unity. In some embodiments, it is greater than five, or even ten.

The female portion's peripheral wall 241 extends longitudinally along the Z-axis, thus forming a suitable cavity for receiving the male portion 230, preferably in its entirety. The cavity extends between an insertion opening that receives the male portion 230 and the orifice 212, which receives the liquid sample. The peripheral wall's internal dimensions are such that the surface of the male portion's perimeter contacts the peripheral wall's internal surface when the female portion 240 accommodates the male portion 230.

The peripheral wall 241 forms a cavity having a cross-section that is complementary to that of the male portion 230. In the illustrated embodiments, the cavity has a substantially rectangular cross-section in the XY-plane to match that of the illustrated the male portion 230.

The second element B also includes the cup-shaped receiving surface 211 that receives the liquid sample. When assembled, orifice 212 discharges at the level of the receiving surface 211.

The receiving surface 211 projects outward relative to the main body's cross section and does so in a direction that is substantially orthogonal to the axis of the female portion 240. The form of the receiving surface 211 is one that promotes bringing the liquid sample to the orifice 212. Exemplary surfaces include a convex surface or one that is flared or curved. Such a shape is particularly useful for capturing a droplet, for example one hanging from the end of a patient's finger and guiding it to the orifice 212. This is often necessary when collecting capillary blood from a fingertip.

After having been deposited on the receiving surface 211, the liquid sample eventually contacts the orifice 212. At that point, capillary action takes over and brings the sample into the channel 231 via its inlet end 232 into the fluid passage 222 that leads to the chamber 221.

To promote capillary action into the passage 231, the walls of the collection device 200 have a wetting angle that is less than ninety degrees and ideally less than fifty degrees. such a wetting angle an be achieved by choosing materials that inherently have such a wetting angle or by chemically treating the surface after having manufactured the first and second elements A, B. Suitable methods of treatment include oxygen-plasma treatment or exposure to high intensity ultraviolet radiation in the presence of oxygen or ozone.

As shown in FIG. 2a, a vent 227 permits the chamber 221 to vent to the atmosphere. The vent 227 is disposed at the level of the end of the chamber 221 opposite the fluid passage 222. The vent 227 has a width that is typically less than that of the chamber 221. In some embodiments, the difference between the vent's width and that of the chamber 221 permits the vent 227 to function as a passive valve.

In some embodiments, analysis is carried out optically by observing an interaction between a beam from the light source and the liquid sample. In these embodiments, the body 220 is transparent to the relevant wavelengths.

In other embodiments, analysis is carried out electrically by observing electrical characteristics of the sample. These embodiments include electrodes disposed in the chamber 221 and connected to a voltage source or current source upon insertion of the body 220 into the housing 120. Such electrodes, and any associated contact tracks, can be formed by thin-film deposition to enable contact with the heelpiece 224.

One way to manufacture the collection device 200, and in particular, the male and female portions 230, 240 thereof, is by injection molding a suitable plastic. Since electromagnetic radiation interacts with the sample, it is particularly useful that the plastic be relatively transparent to the electromagnetic radiation being used. For optical analysis, transparency to infrared or visible light is particularly useful. Suitable plastics for injection molding in these applications include polycarbonate, polypropylene, polyethylene, cyclo-olefin-copolymer (COC), and cyclo-olefin-polymer (COP).

A typical collection device 200 has a length along the Z-axis of on the order of a few centimeters. The receiving surface 211 in such cases defines a cup having an area on the order of a few square centimeters. Embodiments include those in which the receiving surface 211 has a pair of two-centimeter sides and a pair of one-centimeter sides. In such cases, the orifice 212 has a length of a few millimeters, for example, five millimeters, and a width of between one millimeter and a tenth of a millimeter.

The male portion 230 has a length and width on the order of a few millimeters. In some embodiments, the male portion is ten millimeters long and five millimeters wide with a thickness of as low as a few hundred micrometers to as much as a few millimeters. In a particular embodiment, the male portion 230 has a thickness of a single millimeter.

The channel 231 typically has a length of a few millimeters or centimeters and a width of as little as a few hundred micrometers to as much as a few millimeters. The channel's thickness is typically on the order of a few tens of micrometers to a few millimeters.

In a particular embodiment, the chamber 221 as a length, along the Z-axis, of about 6.6 millimeters and a greatest width along the Y-axis of 3 millimeters and a depth, along the X-axis, of 150 micrometers.

The foregoing dimensions are given only by way of illustration.

Figure 3A:
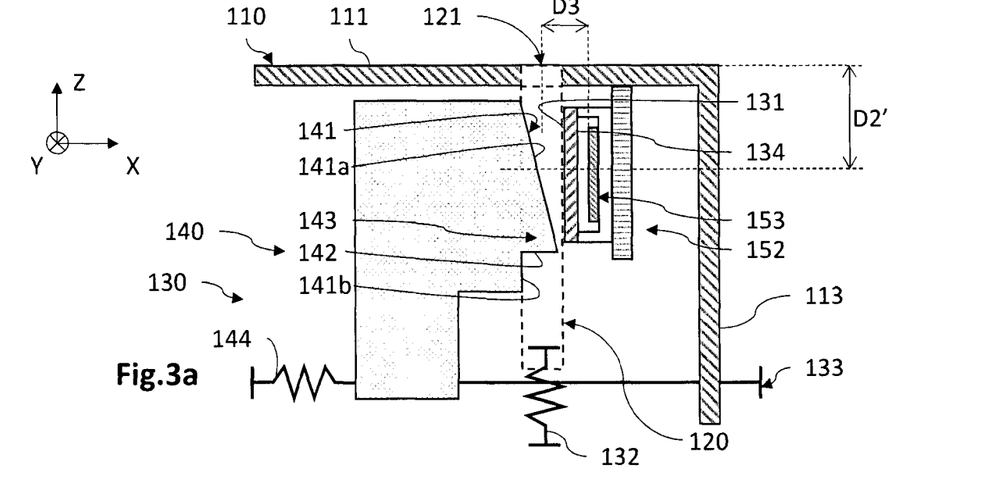
FIGS. 3a to 3c are diagrammatic views looking down the Y, X, and Z axes respectively of the locking and disengagement device.
Figure 3B:
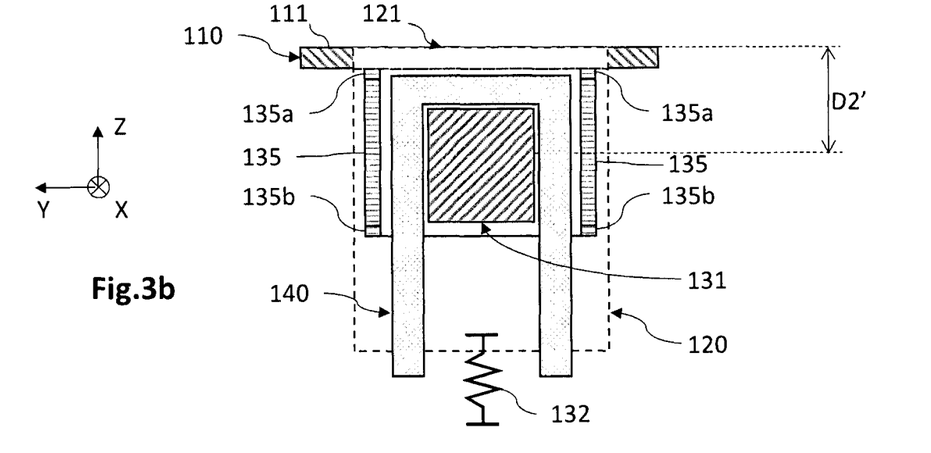
Figure 3C:
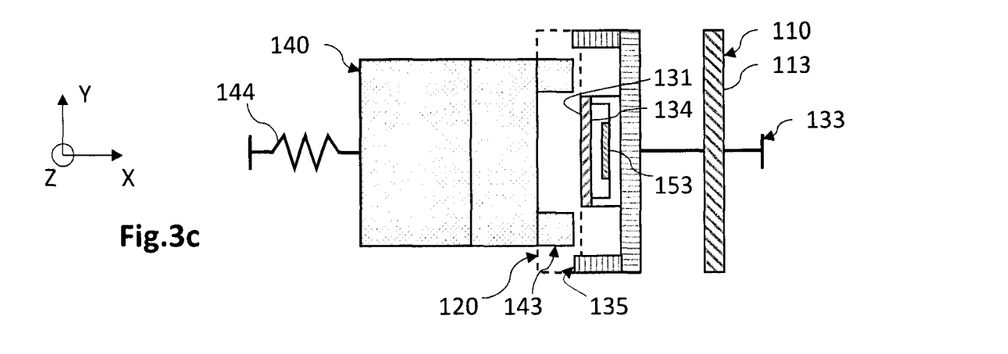

FIGS. 3-3c show views of an analyzer 100 adapted to receive the collection device 200 shown in FIGS. 2a and 2b.

In FIG. 3a, a dashed line indicates the extent of the housing 120. As is apparent from the figure, the housing 120 extends into the interior of the casing 110 from the opening 121. The locking-and-releasing device 130 at least partially delimits the housing 120.

The locking member 140 moves relative to the casing 110 thus bringing its contact surface 141 either toward or away from the housing 120 along the X-axis. A return element 144 exerts a force that urges the locking member 140 towards the housing 120 in the positive direction along the X-axis. In the embodiment shown in FIG. 3a, the return element 144 is a compression spring.

The contact surface 141 includes a spacer portion 141a and a bearing portion 141b.

The spacer portion 141a is an inclined plane that has a proximal edge in the vicinity of the opening 121. The spacer portion 141a extends downward in the negative Z-direction parallel to the insertion axis and with its X-coordinate progressively increasing as a result of its inclination. At a distal edge thereof, the spacer portion 141a has a maximum X-coordinate.

The contact surface 141 continues distally from the distal edge of the spacer portion 141a with the bearing portion 141b.

The bearing portion 141b is a plane having a proximal edge that begins at the Z-coordinate of the distal edge of the spacer portion 141a and proceeds in the negative Z-direction to a distal edge thereof. Unlike the spacer portion 141a, the bearing portion 141b is not an inclined plane. Therefore, its X-coordinate remains constant.

The X-coordinate of the bearing portion 141b is less than the X-coordinate of the spacer portion 141a at its distal edge. This creates a discontinuity that results in an abutment surface that faces in the negative Z direction and that has width equal to the difference between the maximum X-coordinate of the spacer portion 141a and the X-coordinate of the bearing portion 141b. Because of the discontinuity, there exists a step to join the spacer portion 141a and the bearing portion 141b. This step defines an abutment surface 142 of an abutment portion 143. The abutment surface 142 faces distally in the negative Z-direction.

The locking-and-disengagement device 130 also includes an unlocking member 133 and a disengagement member 132.

The unlocking member 133 moves the locking member 140 away from the housing 120, which in FIG. 3a would be in the negative X-direction. This pushes the abutment portion 143 out of the housing 120. In the embodiment shown in FIG. 3a, the unlocking member 133 is a linkage that rigidly connects a pushbutton outside the casing 110 and the locking member 140.

The disengagement member 132 faces the distal end of the housing 122 and exerts an exit force on the collection device 200 along the insertion axis when the collection device 200 is inserted into the housing 122. In FIG. 3a, this exit force would be in the positive Z-direction.

The bearing surface 131 of the locking-and-disengagement device 130 is fixed to the casing 110 so that it cannot move. A suitable bearing surface 131 is a surface of a bearing plate that is fixed along the housing 120 and that extends in a direction parallel to the housing's longitudinal axis. In those embodiments that rely on interaction of light with the sample, the bearing plate is transparent to wavelengths of light relied upon for analysis of the sample so that light can reach an optical sensor 152 disposed on the side of the bearing plate that is opposite the bearing surface 131.

As shown in FIG. 3a, there exists a longitudinal distance D2' and a transverse distance D3.

The longitudinal distance D2' is the distance between the opening 121 and a longitudinal axis of the photodetector 153 of the optical sensor 152. The longitudinal axis of the photodetector 153 is a line that is perpendicular to the surface of the photodetector 153, that extends in the X-direction, and that passes through the center of the photodetector 153, where the center of the photodetector 153 is the intersection of a first and second orthogonal lines that bisect the photodetector 153 along first and second transverse dimensions thereof.

The transverse distance D3 is the shortest distance from a line that extends through the center of the housing 120 in the Z-direction to a point on the surface of detection surface of the photodetector 153.

In a preferred embodiment, the distance D2' is less than or equal to two centimeters and preferably less than or equal to one centimeter. The transverse distance D3 is less than or equal to two centimeters and preferably less than or equal to one centimeter.

FIG. 3b is a view similar to that shown in FIG. 3a but looking down on the YZ-plane along the X-axis. From this point-of-view, it is apparent that the locking member 140 is a U-shaped structure that defines a region through which light traveling in the X-direction is able to reach the photodetector 153 without interference from the locking member 140.

FIG. 3c is a view of the structures shown in FIG. 3a as seen from the Z-axis and looking down at the XY-plane. As can be seen in FIGS. 3b and 3c, in those embodiments that rely on optical detection and analysis, there exists one or more spacer elements 135. In the embodiment shown in FIG. 3c, there are two such spacer elements 135 disposed to be on opposite sides of the bearing surface 131. As a result of the spacer elements 135, the collecting device 200 can be moved away from the bearing surface 131 during insertion and withdrawal thereof.

Each spacer element 135 is a strip that is parallel to the longitudinal axis of the housing 120 and that extends along the entirety of the bearing surface 131 along the Z-direction. Preferably, the spacer element 135 extends as far as the abutment surface 142 of the locking member 140. The longitudinal ends 135a, 135b of the spacer element 135, which can be seen best in FIG. 3b, are beveled to suppress the tendency of the collecting device 200 to jam during insertion or withdrawal thereof.

The strips forming the spacer elements 135 project from the bearing surface 131 by a few hundred micrometers to a few millimeters. In a particularly suitable embodiment, they project by two hundred micrometers.

The existence of such a projection tends to move the collecting device 200 away from the bearing surface 131 during insertion and withdrawal. This avoids the risk of having the collecting device 200 rub against the transparent bearing surface 131 and thus potentially degrading its ability to pass light without interference by, for example, leaving scratches. Such rubbing also results in shear stress that could disturb the spatial relationship between the bearing surface 131 and the bearing plate 134.

In those embodiments that rely on interaction of light with the sample, the transparent bearing surface 131 lies between the housing 120 and the photodetector 153. In some of these embodiments, the bearing surface 131 encapsulates the photodetector 153.

The photodetector detects light from the liquid sample in the chamber 221. Light incident on the photodetector 153 may be light emitted by the liquid sample in response to illumination, for example fluorescent light. Or the light incident on the photodetector 153 may be light that passed through the liquid sample. The light incident on the photodetector 153 can be infrared light, visible light, or ultraviolet light.

A variety of implementations are possible for the photodetector 153. Embodiments include those in which the photodetector 153 is a charge-coupled device and those in which it is a complementary metal oxide semiconductor sensor. In some embodiments, the photodetector 153 is a matrix of detectors that can form an image of the liquid sample.

A variety of implementations are also available for the light source 151. In some embodiments, the light source 151 is a light-emitting diode. In others, it is a laser diode, such as a semiconductor laser diode. Among these are embodiments in which the light source 151 is a vertical cavity surface emitting laser.

In some embodiments, the detection-and-analysis device 150 carries out imaging with no lenses. This is useful when the analytes to be detected are diffracting objects.

For implementation of such embodiments, it is particularly useful that the light source 151 be a source of coherent radiation, such as a laser diode or semiconductor laser diode. Alternatively, a light-emitting diode fitted with a diaphragm can be used to increase coherence of radiation emitted by a light-emitting diode. Or, a light emitting diode with small enough dimensions can be used without a diaphragm. Such a diode would have a diameter less than a tenth of the distance that separates the diode from the housing 120.

The photodetector 153 used to carry out imaging with no lenses is a matrix of detectors so as to acquire images of radiation that is transmitted or diffracted by analytes present in the liquid sample. To promote effective imaging, it is useful to position the photodetector 153 to be displaced by a distance along a line that passes through a central position of the housing 120 and that is parallel to the X-axis. In some embodiments, this distance is between a hundred micrometers and a few centimeters from the housing 120. Embodiments include those in which this distance is less than or equal to one centimeter. It is particularly advantageous for this distance to be within a closed interval that extends from a hundred micrometers to two millimeters. This small distance limits interference between diffraction patterns when illuminating the chamber 221. As a result, it is not necessary to have magnification optics between the housing 120 and the photodetector 153.

Some embodiments feature an array of small lenses, each of which is placed in front of a pixel on the photodetector 153. This causes more light to be incident on a particular pixel but without actually magnifying an image.

Figure 4A:
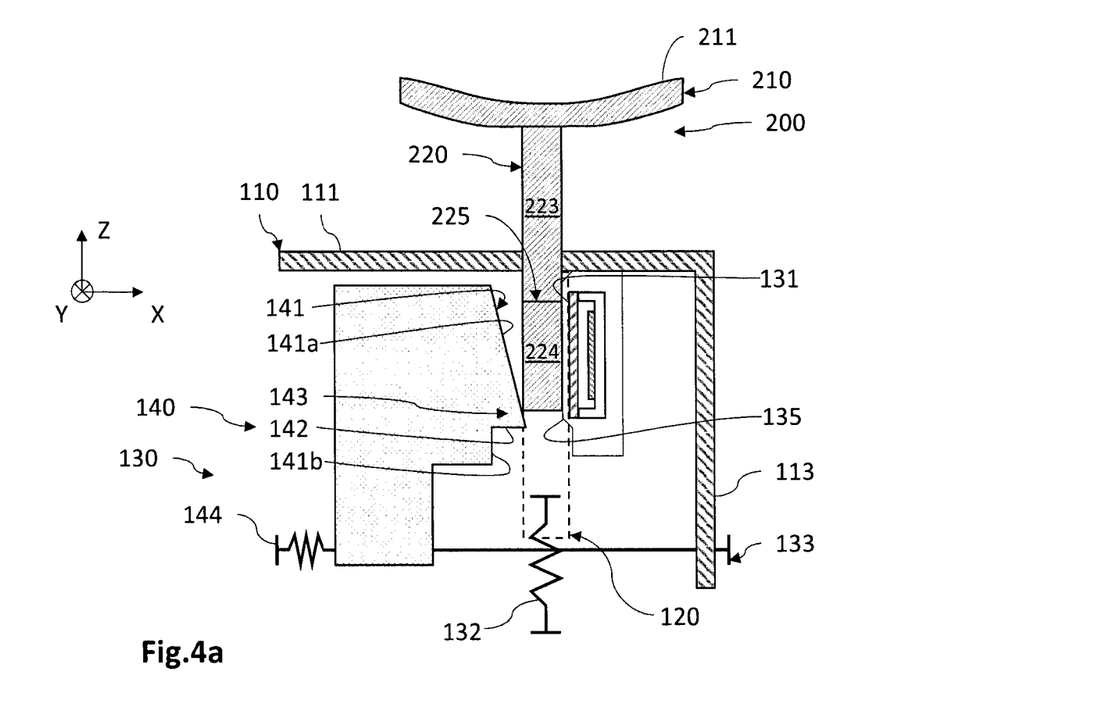
FIG. 4a shows the locking-and-releasing device when the collection device is being inserted.
Figure 4B:
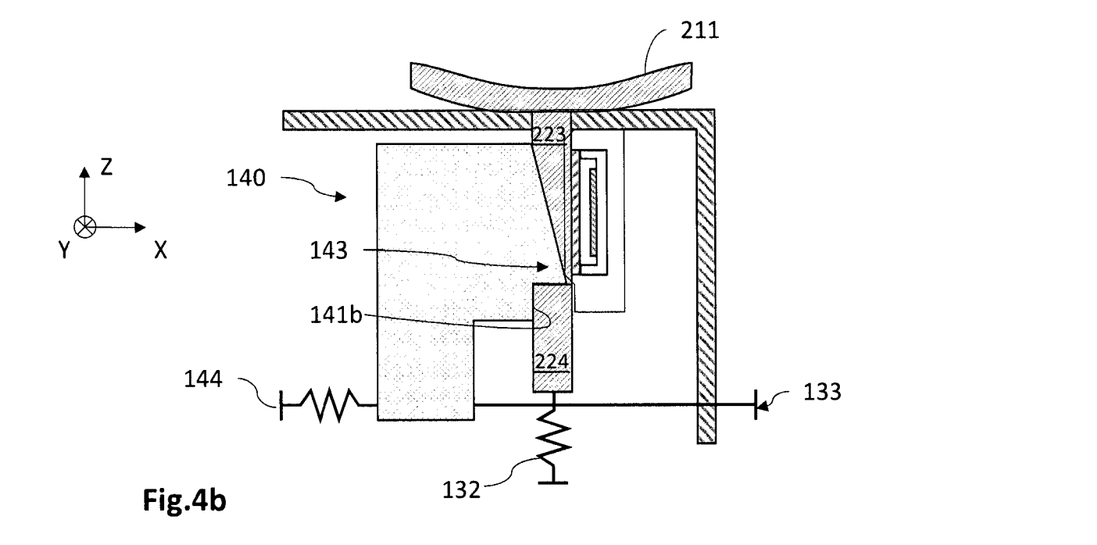
FIG. 4b shows the locking-and-releasing device in its locking position.

FIG. 4a shows the collection device 200 being inserted into the analyzer 100. FIG. 4b shows the collection device 200 after having been inserted into the analyzer 100.

Referring first to FIG. 4a, the heelpiece 224 of the main body 220 comes into contact with the spacer portion 141A of the contact surface 141. As insertion continues, the heelpiece 224 progressively pushes the locking member in the negative X direction. This compresses the spring that forms the return element 144, thus arming the return element 144.

Eventually, the heelpiece 224 reaches the releasing member 132 and compresses another spring that implements the releasing member 132. This arms the releasing element 132 so that it can ultimately apply an exit force to eject the body 220.

As the main body 220 of the collection device 200 makes its way into the housing 120, the spacer elements 135 ensure separation of the main body 220 from the bearing surface 131 until the abutment portion 143 and the bearing portion 225 engage, as shown in FIG. 4b.

As shown in FIG. 4b, the locking position occurs when the main body 220 has moved far enough in the negative Z direction to cause the bearing surface 225 to go past the abutment portion 143. At that point, the return element 144 urges the locking member 140 to move towards the housing 120, thereby engaging the abutment portion 143 with the bearing surface 225.

Meanwhile, the bearing portion 141b of the contact surface 141 exerts a force on the heelpiece 224 in the positive X direction. By this time, the heelpiece 224 no longer contacts the spacer elements 135. This is because, as shown in FIG. 2b, the heelpiece 224 is wider in the Y-direction than the central portion 223 of the main body 220. As a result, the central portion 223 comes into contact with the bearing surface 131.

At this point, the collecting device 200 has been locked so that it cannot move in the Z-direction. The locking occurs as a result of cooperation between the releasing member 132, which exerts a force in the positive Z direction, and the abutment portion 143, which exerts a reaction force in the negative Z direction on the bearing surface 225 of the collecting device 200.

The collecting device 200 is also precluded from moving in the X direction. This is because of the force exerted in the positive X direction by the bearing portion 141b of the contact surface 141 of the locking member 140 against the heelpiece 224 and the reaction force in the negative X direction that results from contact with the bearing surface 131.

As a result, in FIG. 4b, the collection device 200 is locked in the housing 120 relative to the bearing surface 131 so that it cannot move during the detection process. This improves accuracy and reliability, particularly in embodiments that rely on optical methods, and in particular, on embodiments that rely on lens-free imaging.

With the collection device 200 now locked into position and with the receiving surface 211 being oriented perpendicular to the gravity vector, the chamber 221 is now ready to receive a sample.

The process begins with depositing the sample on the receiving surface 211. This sample could be, for example, a drop of blood on a fingertip. In a typical practice, a patient holds the analyzer 100 in hand and presses the receiving surface 211 to dislodge the droplet of blood. The collection device 200 transmits much of the force of this touch to the casing 110, thus avoiding mechanical stresses on the body 220.

The volume of a droplet would be more than sufficient because the chamber 221 is so close to the orifice 212 that the volume of even a droplet is enough to fill the chamber 221.

As a result of capillary action, the liquid sample migrates from the orifice 212 it encounters any dried or freeze-dried reagents that may have been incorporated into the fluid passage 222 or in the chamber 221. In such cases, a chemical reaction may occur that causes a change in color that can then be subjected to colorimetric analysis. For example, the intensity of color is in many cases proportional to the concentration of analytes in the sample.

In some cases, it is possible to carry out lens-free imaging by controlling position and proximity of the sensor 152 relative to the housing 120 by using the bearing surface 131 against which the body 220 is pressed.

In either case, the detection-and-analysis device 150 receives raw data from the photodetector 153 which then displays appropriate information on the display screen 114.

Once detection and analysis have been completed, the collecting device 200 is withdrawn from the analyzer 100. This is carried out by actuating the unlocking member 133. The unlocking member 133 moves the locking member 140 until all mechanical contact between the abutment portion 143 and the bearing portion 225 is eliminated. Once this occurs, the energy stored in the releasing member 132 as a result of having armed the spring moves the body 220 partly out of the housing 120.

In those embodiments that have spacer elements 135, the heelpiece 225 comes into contact with those spacer elements 135 during withdrawal, as a result of which the collecting device 200 no longer contacts the bearing surface 131. This permits free movement without damaging the bearing surface 131.

With the collection device 200 now partly out of the analyzer 100, it is possible to simply turn the analyzer 100 upside-down so that the collection device 200 can drop entirely out of the housing 120 and into a container provided to receive the collection device 200. This permits one to avoid having to actually handle the collection device 200, which may still have trace amounts of the liquid sample.

In some embodiments, the releasing member 132 can store enough energy to completely eject the collection device 200 out of the housing 120.

Figure 5A:
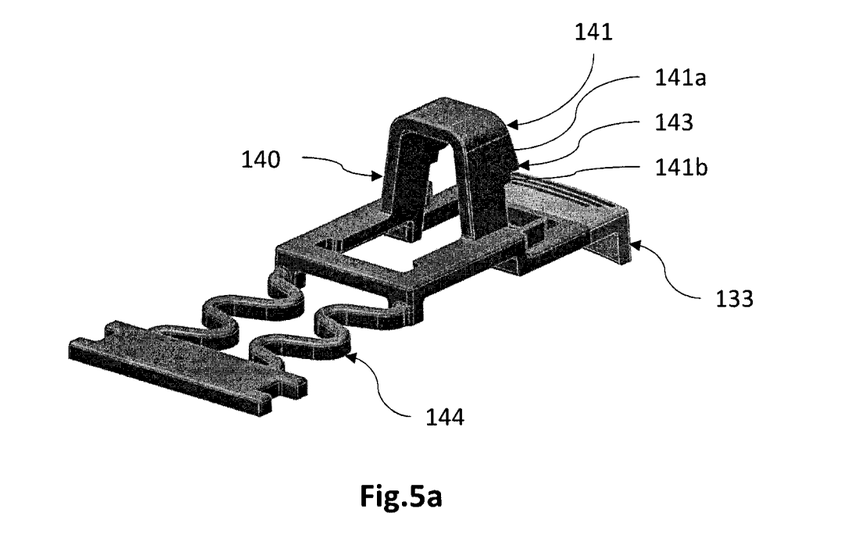
FIGS. 5a and 5b are perspective views of an example of the locking and disengagement device.

FIG. 5a shows a perspective view of one embodiment of a locking-and-releasing device 130 that is formed as a single unitary piece. The figure shows the U-shaped locking member 140 that forms an arched bridge with piers resting on either side of a base that extends rigidly. The unlocking member 133 takes the form of a push-button that compresses the return element 144, which takes the form of a planar compression spring on the side opposite the unlocking member 133.

Figure 5B:
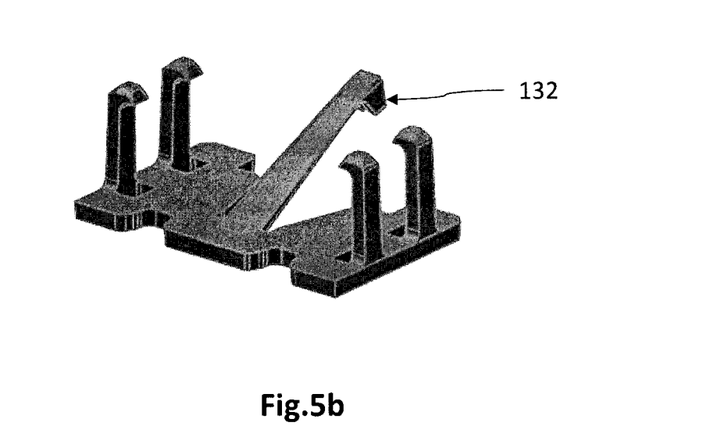

FIG. 5b shows a releasing member 132, which in this implementation takes the form of an inclined flexible blade that, when flattened, stores energy that can be used to exert an exit force on the collection device 200. The releasing member 132 engages under the locking member 140 at the level of the aperture shown in the base in FIG. 5a.

Figure 6:
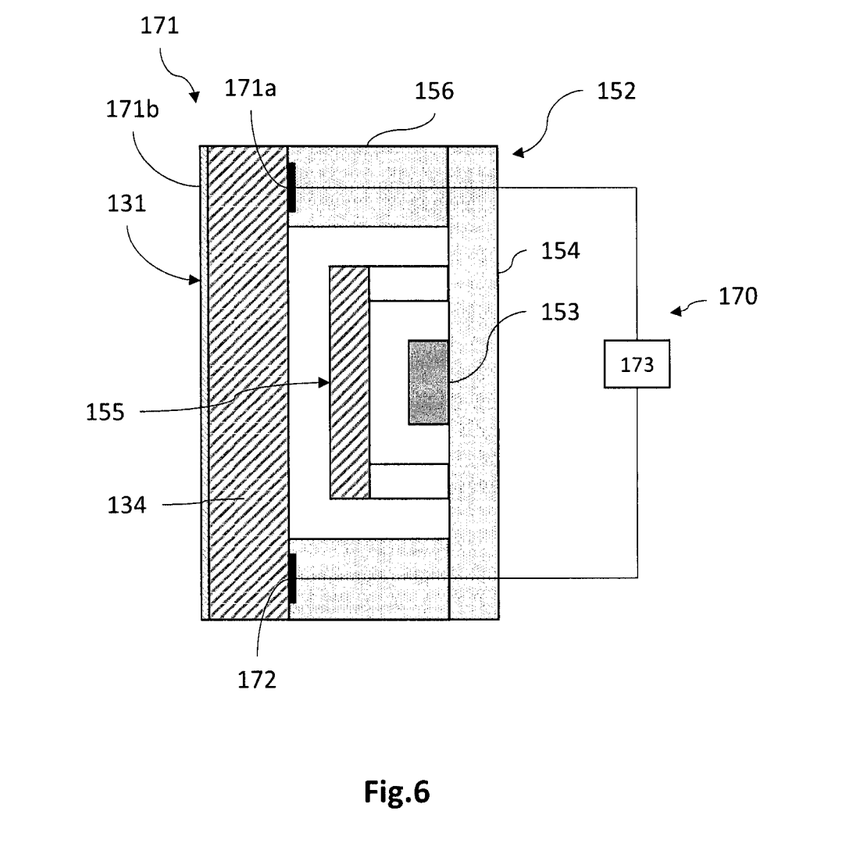
FIG. 6 shows an optical sensor provided with a heating device.

FIG. 6 shows a cross section of an optical sensor 152. A first electronic-card 154 provides power to the photodetector 153 and transmits signals from the photodetector 153 to an analysis unit. A protective cap 155 that is transparent to wavelengths of interest encapsulates the photodetector 153. Examples of a first electronic-card 154 include a printed-circuit board.

To promote a more consistent temperature, a heater 170 thermally regulates the bearing surface 131, and therefore also the central portion 223 of the body 220, which is where the chamber 221 that contains the sample happens to be. A second electronic card 156 provides power to the heating device 170. Examples of a first electronic-card 156 include a printed-circuit board. The bearing surface 131 rests on the second electronic-card 156.

The heater 170 includes a heating element 171, a temperature probe 172, and a thermal regulator 183 that is electronically connected to both the heating element 171 and the temperature probe 172.

The heating element 171 emits heat using the Joule effect. This heat flows to the central portion 223 of the body 220 when the central portion 223 contacts the bearing surface 131. In some embodiments, an electrically-conductive track, such as a metal track 171a connects to an electrically-conductive and preferably transparent layer 171b that heats in response to current. In the illustrated embodiment, the metal track 171a lies between the bearing plate 134 and the second electronic card 156.

The conductive layer 171b shown in FIG. 6 is disposed at the level of the bearing plate 134 and oriented towards the housing 120. As such, it forms a part of the bearing surface 131. Alternatively, the conductive layer 171b can also be on the opposite face of the bearing plate 134.

In some embodiments, the conductive layer 171b is a layer of transparent material, such as amorphous silicon or indium-tin oxide screen printed or sprayed onto the surface of the bearing plate 134. A current source provides current for heating via an electronic card 154, 156. The regulator 173 controls this current source in response to a signal received from the temperature probe 172.

The temperature probe 172 is positioned as closely as possible to the bearing surface 131 and connected to the thermal regulator 173 to provide it with a measured temperature upon which to base control over the current at the metal track 171a.

In some embodiments, the heating element 171 includes the bearing plate 134 and the metal track 171a in combination. In this case, the bearing plate 134 comprises a thermally-conductive material that is transparent at the wavelengths of interest. An example of such a material is sapphire. In these embodiments, it is possible to omit the conductive layer 171b.

The regulator 173 connects to both the metal track 171a and the temperature probe 172. The regulator 183 compares the measured temperature as provided by the temperature probe 172 with a setpoint and then causes the current source to provide a current that, when passed through the metal track 171a, will drive the temperature towards the set point.

The heater 170 enables permits the liquid sample in the chamber 221 to be maintained at a fixed temperature. Thus, in addition to supporting the central portion 223, the bearing surface 131 also makes it possible to thermally regulate the chamber 221.

Particular embodiments have just been described. Different variants and modifications will be apparent to the person skilled in the art.

Thus the detection device may provide electrochemical detection of one or more properties of the liquid sample instead of or in addition to optical detection. To this end the measuring chamber may be equipped with one or more electrodes. When the collecting device is inserted in the analysis device, these electrodes can come into contact with electric contact studs, for example, positioned at the level of the bearing surface, these studs being electrically connected to a voltage or current source. Thus a potential difference or a current can be applied to the electrodes and an electrochemical property of the liquid can be detected and then analyzed.

The invention claimed is:

1. An apparatus for analyzing a liquid sample, said apparatus comprising an analyzer and a collection device,
   wherein said analyzer comprises a casing, a housing, and a detection-and-analysis device,
   wherein said casing delimits an interior space,
   wherein said casing comprises an opening that leads into said housing,
   wherein said housing is adapted to receive a portion of said collection device,
   wherein said housing is disposed in said interior space,
   wherein said housing extends from said opening along an insertion axis,
   wherein said detection-and-analysis device is configured to detect and analyze a representative parameter of said liquid sample,
   wherein said collection device comprises a main body, a receiving surface, a chamber, and a collecting orifice, wherein said main body extends along a longitudinal axis from said receiving surface to said chamber and is adapted to be longitudinally inserted into said housing along said insertion axis, wherein, when said main body has been inserted into said housing, said longitudinal axis is parallel to said insertion axis, wherein, when said main body has been inserted into said housing, said receiving surface remains outside said housing to receive said liquid sample, wherein said receiving surface extends beyond an area of said main body and at least orthogonally to said longitudinal axis of said main body, and wherein said collection orifice provides fluid communication into said chamber along said longitudinal axis.

2. The apparatus of claim 1, wherein, when said main body has been inserted into said housing, the main body is located inside the housing, the collection device contacts the casing, and a fluid passage connects the collecting orifice to the chamber, wherein the fluid passage separates the collecting orifice from the chamber by a distance that is approximately equal to the distance between the opening of the housing and the chamber.

3. The apparatus of claim 1, wherein the collection device comprises a collecting portion assembled to the main body, wherein a surface of said collecting portion forms the receiving surface, wherein the collecting portion contacts a wall of the casing at an edge of the opening of the housing when the main body of the collection device has been inserted into the housing, wherein said collecting portion projects transversely from said main body, wherein said orifice opens into a fluid passage that passes through said collecting portion and connects said orifice to said chamber so that liquid migrates from the orifice and into the fluid passage.

4. The apparatus of claim 1, wherein the casing comprises an upper wall and a lower wall connected to each other by a lateral wall having a dimension that is less than the dimensions of the upper and lower walls, wherein the opening is situated at the upper wall of the casing, and wherein the housing extends substantially orthogonally to the upper wall in the direction of the lower wall.

5. The apparatus of claim 4, further comprising a display screen that is disposed on said upper wall.

6. The apparatus of claim 1, wherein said analyzer further comprises a bearing surface that is fixed relative to the housing, wherein said bearing surface is disposed so as to delimit in part the housing by extending parallel to the insertion axis, wherein, when said main body has been inserted into said housing, said bearing surface contacts that portion of said main body that contains said chamber.

7. The apparatus of claim 6, wherein the detection-and-analysis device comprises an optical sensor situated on a side of the bearing surface opposite the housing, the bearing surface being transparent to light beams coming from the chamber when the main body of the collection device is inserted in the housing.

8. The apparatus of claim 6, wherein said analyzer further comprises a spacer disposed longitudinally along a border of the bearing surface and projecting relative to the bearing surface-in the direction of the housing, wherein said spacer has longitudinal ends that are beveled so as to space the main body relative to the bearing surface upon movement of the bearing surface in the housing along the insertion axis.

9. The apparatus of claim 6, further comprising an optical reader for reading information on said main body, said reader comprising a light source and a matrix photodetector.

10. The apparatus of claim 1, wherein the detection-and-analysis device comprises an optical sensor situated at a longitudinal distance relative to the opening of the housing, wherein said longitudinal distance is less than or equal to two centimeters.

11. The apparatus of claim 1, wherein said analysis device further comprises a locking-and-disengagement device that is adapted to retain the main body in a locking position inside the housing, wherein said locking-and-disengagement device comprises a disengagement member and a locking member, wherein said disengagement member is adapted to exert an exit force on the main body when the main body is inserted into the housing in a direction parallel to the insertion axis of the housing and oriented toward the opening of the housing, wherein the locking member comprises at least one abutment portion adapted to be in contact with a bearing portion of the main body when the main body is inserted into the housing in the locking position so as to immobilize the collection device, which becomes subjected to the exit force along the insertion axis.

12. The apparatus of claim 11, wherein the main body comprises a lateral shoulder that forms the bearing portion of the main body of the collection device, wherein said lateral shoulder is situated between a central portion of the main body and a distal end of the main body, wherein said central portion contains the chamber and wherein said distal end of the main body is distal relative to the receiving surface.

13. The apparatus of claim 11, wherein the locking member is mobile relative to the housing along a direction that is substantially transverse to the insertion axis and wherein the locking member is adapted to exert a bearing force on the main body in the direction of the bearing surface when the main body is inserted in the housing.

14. The apparatus of claim 11, wherein the locking-and-disengagement device comprises an unlocking member that, when actuated, causes movement of the locking member so as to break an abutment between the abutment portion of the locking member and the bearing portion of the collection device, thereby leading to withdrawal of the main body relative to the housing by the effect of the exit force.

15. The apparatus of claim 11, wherein the detection-and-analysis device comprises a light source and an optical sensor disposed on respective opposite sides of the housing along an axis of illumination of the chamber when the main body of the collection device is inserted into the housing and wherein the locking member comprises a hollow portion positioned between the light source and the optical sensor, whereby illumination beams propagate along the illumination axis through said hollow portion.

16. The apparatus of claim 1, further comprising a heating element adapted to transmit heat to the chamber via the bearing surface when the main body is inserted into the housing and in contact with the bearing surface.

17. The apparatus of claim 1, wherein the detection-and-analysis device comprises an optical sensor situated at a transverse distance relative to the housing, wherein the transverse distance is less than or equal to two centimeters.

18. The apparatus of claim 1, wherein, when said main body has been inserted into said housing, there exists a first plane and a second plane parallel to the first plane, wherein there exists a distance between the first and second planes, wherein the first plane is a plane that includes the collecting orifice, wherein the second plane is a midplane of the measurement chamber, and wherein the distance is less than or equal to two centimeters.

19. The apparatus of claim 1, wherein the chamber comprises electrodes that receive electrical power when said collection device is inserted into said housing.

20. A method for analyzing a liquid sample using an analyzer and a collection device comprising,
- providing the apparatus of claim 1,
- introducing said main body of the collection device into the housing,
- depositing said liquid sample on the receiving surface of the collection device so that said liquid sample is in contact with the collecting orifice, and
- detecting and analyzing a representative parameter of the liquid sample.

* * * * *